United States Patent [19]

Nielsen et al.

[11] Patent Number: 4,849,220
[45] Date of Patent: Jul. 18, 1989

[54] USE OF BORON SUPPLEMENTS TO INCREASE IN VIVO PRODUCTION OF HYDROXYLATED STEROIDS

[75] Inventors: Forrest H. Nielsen; Curtiss D. Hunt, both of Grand Forks, N. Dak.

[73] Assignee: The United States of America as represented by the Secretary of Agriculture, Washington, D.C.

[21] Appl. No.: 183,810

[22] Filed: Apr. 20, 1988

[51] Int. Cl.$^4$ ............................................. A61K 33/22
[52] U.S. Cl. ..................................... 424/659; 424/660
[58] Field of Search ......................................... 424/148

[56] References Cited

FOREIGN PATENT DOCUMENTS 2103088  2/1983  United Kingdom ................ 424/148

OTHER PUBLICATIONS

Merck Index, #8421, Tenth Ed., 1983.
Forrest H. Nielsen, "Effects of Dietary Boron, Aluminum, and Magnesium on Plasma Alkaline Phosphatase, Calcium, Phosphorus, Cholesterol . . . , " Abstract, Third Conference for Federally Supported Human Nutrition Research Units and Centers, 1987.
Forrest H. Nielsen et al., "Effect of Dietary Boron on Mineral, Estrogen, and Testosterone Metabolism in Postmenopausal Women," FASEB J. 1: 394–397, (1987).
Judy McBride, "Banishing Brittle Bones with Boron?" Agricultural Research, Nov./Dec. 1987, pp. 12–13.
Terrence R. Shuler et al., "Interactions Among Boron, Calcium, and Magnesium in Rats: Plasma and Bone Mineral Content," Abstract 91, Proc. North Dakota Acad. Sci. 40: 81, (Apr. 1986).
Forrest H. Nielsen, "Boron Affects Magnesium Deprivation and Aluminum Toxicity in Rats," Abstract 92, Proc. North Dakota Acad. Sci. 40: 82, (Apr. 1986).
C. D. Hunt et al., "Dietary Boron Affects Molybdenum and Magnesium Metabolism in the Cholecalciferol Deficient Chick," Abstract 93, Proc. North Dakota Acad. Sci., 40: 83, (Apr. 1986).
Forrest H. Nielsen, "Other Elements: Sb, Ba, B, Br, Cs, Ge, Rb, Sr, Sn, Ti, Zr, Be, Bi, Ga, Au, In, Nb, Sc, Te, Tl, W," In Trace Elements in Human & Animal Nutrition, vol. 2, Academic Press, New York, pp. 420–427, 454–463, (1986).
Rex E. Newnham, "Mineral Imbalance and Boron Deficiency," In Trace Element Metabolism in Man and Animals, 4: 400–402, Aust. Acad. Sci. Canberra, (1981).
J. A. Jansen et al., "Gastro–Intestinal Absorption and in vitro Release of Boric Acid from Water–Emulsifying Ointments," Fd. Chem. Toxic, 22(1): 49–53, (1984).
C. A. Zittle, "Reaction of Borate with Substances of Biological Interest," In Advances in Enzymology, vol. XII, pp. 493–527, F. F. Ford (ed.), Interscience Publishers, New York, (1951).

Primary Examiner—Douglas W. Robinson
Assistant Examiner—Roger Gobrogge
Attorney, Agent, or Firm—M. H. Silverstein; J. D. Fado; M. E. Brokke

[57] ABSTRACT

The oral administration of boron compounds such as sodium borate and boric acid increases the amounts of hydroxylated steroids in human plasma. This will help prevent or alleviate pathology, such as osteoporosis, caused by suboptimal circulating hydroxylated steroids such as 17$\beta$-estradiol and testosterone.

2 Claims, No Drawings

USE OF BORON SUPPLEMENTS TO INCREASE IN VIVO PRODUCTION OF HYDROXYLATED STEROIDS

BACKGROUND OF THE INVENTION

The previously known effects of boron on animal metabolism have been reviewed by Nielsen ["Trace Elements in Human and Animal Nutrition," Vol. 2, pp. 422-427, Academic, New York (1986)].

In 1981, Hunt and Nielsen [In "Trace Element Metabolism in Man and Animals-4," pp. 597-600, Aust. Acad. Sci., Canberra (1981)]reported that boron deprivation depressed growth and elevated alkaline phosphatase activity in chicks fed inadequate cholecalciferol. Cholecalciferol deficiency enhanced the need for boron, and it was postulated that boron might interact with the metabolism of calcium, phosphorus, or magnesium.

Further experiments suggested that the influence of boron was the result of altered parathormone activity [F. H. Nielsen, In "Trace Elements in Man and Animals-5 Abstracts," p. 26, Aberdeen, Scotland (1984)]. This hypothesis was also supported by Elsair et al. [Fluoride 15: 30-38 (1980)], who reported that high dietary boron partially alleviated the fluoride-induced secondary hyperparathyroid signs of hypercalcemia in rabbits.

Further indications of a relationship between boron and calcium are that boron or boron compounds can influence calcium metabolism and that boron levels change in animals with abnormal calcium metabolism. Amine cyanoboranes and amine carboxyboranes effectively block induced arthritis [I. H. Hall et al., J. Pharm. Sci. 69: 1025-1029 (1980)], and tablets containing magnesium carbonate and sodium borate have been sold as a remedy for arthritis. This effect was thought to be attributable to changed ATP metabolism at the cell membrane level to cause cell division and regeneration [R. E. Newnham, In "Trace Element Metabolism in Man and Animals-4," pp. 400-402, Aust. Acad. Sci. Canberra (1981)].

Estrogens are known to exert profound effects on the metabolism of calcium and phosphorus as well as lipids and proteins in the human body. Administration of estrogen hormones in man decreases the level of circulating blood lipids; this effect has drawn attention to a possible role of sex hormones in atherosclerosis.

Estrogen therapy is used to alleviate the symptoms of bone decalcification seen in postmenopausal osteoporosis. However, prolonged estrogen administration may result in elevation of serum calcium and phosphate levels, with calcification and hyperossification of the long bones, so that the marrow cavity may disappear and result in anemia. [See A. White et al., "Principles of Biochemistry," McGraw-Hill, New York, p. 858 (1964).]

SUMMARY OF THE INVENTION

We have now unexpectedly discovered that addition of boron-containing compounds to the diet of postmenopausal women results in an increased production of hydroxylated steroids including 17-$\beta$-estradiol and testosterone.

In accordance with this discovery, it is an object of this invention to provide a new method for increasing estrogen production in animals.

It is a further object of this invention to provide a new method for increasing testosterone production in animals.

It is also an object of this invention to provide a new and unobvious use for boron-containing compounds.

Other objects and advantages of this invention will become apparent from the ensuing description.

DETAILED DESCRIPTION OF THE INVENTION

It has been unexpectedly observed that the oral administration of boron-containing compounds such as sodium borate and boric acid at levels of 1 to 10 mg per day will increase the amount of circulating biologically active hydroxylated steroids in animal plasma.

As a practical matter, it will be evident that other relatively nontoxic boron compounds will be effective in this invention. These would include, but would not be limited to, pharmaceutically acceptable salts of boric acid and other relatively nontoxic organoborane compounds. An effective or pharmaceutically effective amount is herein defined as an amount of a boron-containing compound which causes a statistically significant increase in hydroxylated steroids in a test animal.

Those skilled in the art will recognize that the mode of administration may be varied to include oral, dermal, and injection applications. When administered orally, the boron-containing compound may be incorporated in food or beverage material. Alternatively, it may be manufactured into pills or tablets with a suitable diluent or carrier using known techniques. In dermal and injection applications, it will be obvious to dilute the boron-containing compound with a carrier suitable for these uses. Dose rate may be varied according to the degree of stimulation of hydroxylated steroid production desired and by the toxicity and biological activity of the particular boron compound selected for administration.

It is envisioned that boron compounds will find utility in treating hydroxylated steroid deficiency in animals. This will be useful, for example, in the treatment of osteoporosis and other symptoms of estrogen deficiency in postmenopausal women.

Boron-containing compounds may also be used in treating normal agronomically important animals to increase the rate of output productivity. For example, in meat-producing animals, it will be possible to increase the rate of protein accretion and other edible tissues and to reduce the time of rearing prior to market. Likewise, it is envisioned that the inventive process would be operative in enhancing other performance or product outputs, such as fertility, lactation in mammals, egg production in layer hens, performance of work in draft animals, and synthesis of natural fiber in wool- and fur-bearing animals.

In the preferred method of this invention, test subjects were administered 3 mg of sodium borate/day in divided doses at meal times for two 24-day dietary periods. This resulted in markedly elevated serum concentration of 17$\beta$-estradiol and testosterone. This effect of boron became evident about 8 days after boron supplementation began and remained relatively constant throughout the test period.

The data in Table I indicate that dietary boron had a marked effect on major mineral metabolism in the postmenopausal women. This effect apparently was modified by magnesium status, but not by the ingestion of 1000 mg of aluminum/day. The data show that supplements of 3.0 mg of boron/day fed to postmenopausal women, who had been consuming 0.25 mg of boron/day for 119 days, markedly reduced their urinary excretion of calcium and magnesium. Although the experimental design prevented a direct examination of the effect of magnesium status on the response to dietary boron, the differences in excretion seemed to be more marked in the low-magnesium than in the adequate-magnesium women. For example, the reduction of urinary calcium excretion caused by boron supplementation was 52 mg/day in the low-magnesium women and 22 mg/day in the adequate-magnesium women. Urinary phosphorus excretion was reduced by boron supplementation in the low-magnesium women but not in the adequate-magnesium women.

The data in Table II indicate that the findings attributed to boron were not spurious effects caused by the passage of time under the described environmental conditions. As the experiment progressed, there was no gradual decrease in the urinary excretion of calcium and magnesium, nor a gradual increase in the serum concentration of $17\beta$-estradiol and testosterone. All of these variables changed abruptly, regardless of dietary aluminum and magnesium, about 8 days after boron supplementation began. The equilibration values in Table 2 suggest that low-dietary boron decreases serum $17\beta$-estradiol and testosterone.

The data in Table III, which does not include one test subject on estrogen therapy, show that a supplement of 3.0 mg of boron/day fed to postmenopausal women who had been consuming 0.25 mg boron/day for 119 days markedly elevated the serum concentration of $17\beta$-estradiol and testosterone. Similar to the changes in urinary excretion of minerals, the elevation in serum steroids seemed more marked in the low-magnesium women. Although it was not significant, aluminum supplementation tended to reduce the steroid response of the adequate-magnesium women to boron supplementation.

Without desiring to be bound to any particular theory of operation, it is believed that boron changes the amount of circulating hormones in mammals through regulation of the hydroxylation of steroid precursors.

The following examples are intended only to further illustrate the invention and are not intended to limit the scope of the invention which is defined by the claims.

EXAMPLE 1

Selection of Test Subjects and Diets

The study was done with 13 postmenopausal Caucasian women between ages 48 and 82. Two of the women were on estrogen therapy throughout the study. After medical, psychological, and nutritional evaluation established that they were in good health and emotionally suited for the study, each volunteer signed an informed consent after receiving both oral and written presentations of the nature of the research. The study protocol was approved by the Institutional Review Board of the University of North Dakota and the Human Studies Committee of the U.S. Department of Agriculture. The protocol followed the guidelines of the Department of Health and Human Services and the Helsinki Doctrine regarding the use of human subjects.

The women, who lived in a metabolic unit under close supervision for 167 days, were fed a 3-day menu rotation diet composed of conventional foods including beef, pork, rice, bread, and milk, but low in fruits and vegetables. To ensure adequacy, supplements were used to provide the indicated additional amounts of the following nutrients per day: potassium, 630 mg as potassium chloride; calcium, 135 mg as calcium gluconate; copper, 0.8 mg as cupric sulfate; iron, 18 mg as ferrous gluconate; cholecalciferol, 400 IU; and folic acid, 200 $\mu$g. All supplements were given at mealtimes. The kilocalorie intake of each volunteer was based on her energy needs as calculated with the Harris and Benedict equation ["A Biometric Study of Basal Metabolism in Man," Carnegie Institute of Washington Publ. No. 279, Philadelphia: Lippincott (1919)], plus an additional 50% of basal energy expenditure for normal activity. To achieve the appropriate energy intake, all menu ingredients were increased or decreased proportionally in 200-kcal increments. The range of energy intakes among the subjects was 1600–2400 kcal. During the study, energy intake was adjusted to maintain body weight within 2% of admission weight. The diet contained 14% protein, 47% carbohydrate, and 39% fat. At an intake of 2000 kcal, the diet provided per day (as determined by analysis): 600 mg calcium, 870 mg phosphorus, 116 mg magnesium, 0.25 mg boron, and <0.10 mg aluminum. The diet samples were prepared by our usual methods for elemental analysis using inductively coupled plasma emission spectrometry.

EXAMPLE 2

Dietary Periods

After an equilibration period of 23 days during which the basal low-boron diet supplemented with 200 mg of magnesium/day was fed, all women participated in four dietary periods of 24 days. These periods were: (1) basal diet only; (2) basal diet supplemented with 1000 mg aluminum as aluminum hydroxide/day; (3) basal diet supplemented with 200 mg of magnesium as magnesium gluconate/day; and (4) basal diet supplemented with 1000 mg of aluminum and 200 mg of magnesium/day. The treatments were arranged in a Latin square design and the supplements were fed in a double-blind fashion. The supplements were given in divided doses at mealtimes.

EXAMPLE 3

Boron Supplemental Diet

Upon completion of these four 24-day dietary periods and the prior equilibration period, the volunteers were fed a diet low in boron for 119 days. After completing this phase of the study, 12 women, including only 1 on estrogen therapy, participated in two additional 24-day dietary periods in which the basal diet was supplemented with 3 mg of boron as sodium borate/day in divided doses at mealtimes. Seven women, including the one on estrogen therapy, were fed: (1) the boron basal diet only, and (2) the boron basal diet supplemented with 1000 mg of aluminum/day; thus, these women were fed a diet low in magnesium for the full 48 days. The other five women were fed: (1) the boron basal diet supplemented with 200 mg of magnesium/day, and (2) the boron basal diet supplemented with 200 mg of magnesium and 1000 mg of aluminum/day.

EXAMPLE 4

Analytical Methods

All urine excreted daily was collected with care each morning at 8:00 a.m. Urine was collected in plastic containers containing 6 ml of 3 M hydrochloric acid. Urinary calcium and magnesium were determined by using standard atomic absorption methodology. Urinary phosphorus was determined by using the method of Fiske and Subbarow [J. Biol. Chem. 66: 375–400 (1925)]. Urine samples from the last 20 days of each 24-day dietary period were used to obtain the means given in Tables I and II.

Blood was drawn using standard phlebotomy techniques between 6:00 and 7:00 a.m. after 10 hr of fasting. Serum was obtained on days 16 and 24 in each 24-day dietary period for the radioimmunoassay determination of 17$\beta$-estradiol and testosterone. The standard kits used for analyses (Radioassay System Laboratories, Carson, CA) detected the total unconjugated form of testosterone and 17$\beta$-estradiol. The test for 17$\beta$-estradiol did not distinguish between the free and protein-bound states of this most biologically active form of naturally produced human estrogen.

It is understood that the foregoing detailed description is given merely by way of illustration and that modifications and variations may be made therein without departing from the spirit and scope of the invention.

TABLE I

Effect in Postmenopausal Women of Boron and Aluminum on Urinary Excretion of Calcium, Magnesium, and Phosphorus

| Dietary treatment, mg/day | | Urinary excretion, g/24 hr | | | | | |
|---|---|---|---|---|---|---|---|
| | | Low-Mg diet[a] | | | Adequate-Mg diet[b] | | |
| B | Al | Ca | Mg | P | Ca | Mg | P |
| 0.25 | 0 | 0.117 ± 0.014 | 0.069 ± 0.005 | 0.67 ± 0.04 | 0.132 ± 0.038 | 0.111 ± 0.015 | 0.65 ± 0.06 |
| 0.25 | 1000 | 0.124 ± 0.018 | 0.071 ± 0.005 | 0.69 ± 0.02 | 0.128 ± 0.035 | 0.097 ± 0.009 | 0.73 ± 0.06 |
| 3.25 | 0 | 0.065 ± 0.006 | 0.050 ± 0.008 | 0.54 ± 0.02 | 0.104 ± 0.035 | 0.083 ± 0.012 | 0.67 ± 0.07 |
| 3.25 | 1000 | 0.073 ± 0.011 | 0.047 ± 0.005 | 0.59 ± 0.03 | 0.113 ± 0.041 | 0.089 ± 0.014 | 0.64 ± 0.06 |
| | | Analysis of variance, P values | | | | | |
| Boron | | 0.0004 | 0.0004 | 0.003 | 0.001 | 0.004 | NS |
| Aluminum | | NS | NS | NS | NS | NS | NS |
| Boron × aluminum | | NS | NS | NS | NS | NS | NS |

[a]Average excretion of seven women ± SEM during the last 20 days of each dietary period.
[b]Average excretion of five women ± SEM during the last 20 days of each dietary period.

TABLE II

Changes in Urinary Excretion of Calcium, Magnesium, and Phosphorus and of Serum 17 $\beta$-Estradiol and Testosterone by Dietary Period

| | Dietary period[a] | | | | | | |
|---|---|---|---|---|---|---|---|
| | | Low boron | | | | High boron | |
| Variable | Equilibrium[b] | 1 | 2 | 3 | 4 | 5 | 6 |
| Urinary Ca, g/24 hr | 0.126 | 0.124 | 0.109 | 0.125 | 0.127 | 0.090 | 0.081 |
| | | A[c] | AB | A | A | B | B |
| Urinary Mg, g/24 hr | 0.110 | 0.089 | 0.094 | 0.079 | 0.095 | 0.074 | 0.054 |
| | | A | A | AB | A | AB | B |
| Urinary P, g/24 hr | 0.61 | 0.66 | 0.61 | 0.70 | 0.52 | 0.59 | 0.61 |
| | | AB | AB | A | B | AB | AB |
| Serum 17 $\beta$-estradiol,[d] pg/ml | 23.9 | 11.9 | 15.0 | 26.9 | 12.7 | 35.9 | 37.5 |
| | | A | A | AB | A | B | B |
| Serum testosterone,[d] ng/ml | 0.60 | 0.34 | 0.31 | 0.33 | 0.30 | 0.71 | 0.64 |
| | | A | A | A | A | B | B |

[a]After an equlibration period of 23 days when dietary boron was 0.25 mg/day there were six 24-day dietary periods. In the first four periods, magnesium and aluminum were varied using a Latin square design, and boron was kept at 0.25 mg/day. In the last two dietary periods, boron was increased to 3.25 mg/day. In these two periods, seven women were not supplemented with magnesium, five women were fed a supplemental 200 mg of magnesium/day, and dietary aluminum varied. The six dietary periods are listed sequentially according to time and without regard to different dietary treatments.
[b]Urinary excretion values represent the mean of 13 women during day 7–9 of the equilibration period, serum 17 $\beta$-estradiol and testosterone values represent the mean of 12 women on day 23 of the equilibration period.
[c]Values above the same letters are not significantly different (P > 0.05) as determined by Scheffe contrasts. The equilibration period was not included in the statistical analysis.
[d]Means do not include values from one woman who was treated with estrogen.

TABLE III

Effect in Postmenopausal Women of Boron and Aluminum on Serum Concentrations of 17 $\beta$-Estradiol and Testosterone

| Dietary treatment, mg/day | | Low-Mg diet | | Adequate-Mg | |
|---|---|---|---|---|---|
| | | 17 $\beta$-Estradiol[a] | Testosterone,[a] | 17 $\beta$-Estradiol,[b] | Testosterone,[b] |
| B | Al | pg/ml | ng/ml | pg/ml | ng/ml |
| 0.25 | 0 | 21.1 ± 6.5 | 0.31 ± 0.06 | 15.5 ± 5.4 | 0.38 ± 0.09 |
| 0.25 | 1000 | 17.8 ± 4.2 | 0.34 ± 0.06 | 24.6 ± 7.9 | 0.33 ± 0.05 |
| 3.25 | 0 | 41.4 ± 12.1 | 0.83 ± 0.09 | 38.0 ± 1.5 | 0.65 ± 0.05 |
| 3.25 | 1000 | 38.5 ± 5.9 | 0.66 ± 0.10 | 29.9 ± 2.5 | 0.56 ± 0.05 |
| | | Analysis of variance, P values | | | |
| Boron | | 0.01 | 0.0008 | 0.03 | 0.02 |
| Aluminum | | NS | NS | NS | NS |
| Boron × aluminum | | NS | NS | NS | NS |

[a]Average serum concentration of six women ± SEM on days 16 and 24 of each dietary period. Means do not include values from one woman who was treated with estrogen.
[b]Average serum concentration of five women ± SEM on days 16 and 24 of each dietary period.

We claim:

1. A method of incresing the amount of 17β-estradiol or testosterone produced by a post-menopausal woman comprising administering to said woman a therapeutically effective amount of boric acid or a pharmaceutically acceptable salt of boric acid.

2. A method for treating the symptoms of estrogen deficiency in post-menopausal women comprising orally administering to said women boric acid or sodium borate in an amount of about 1 to 10 mg per day, said boric acid or sodium borate being in sufficient quantity to cause a statistically significant increase in serum concentration of 17β-estradiol or testosterone in said women.

* * * * *